(12) United States Patent
Klatzmann et al.

(10) Patent No.: US 6,333,171 B1
(45) Date of Patent: Dec. 25, 2001

(54) CD4 GENE REGULATORY SEQUENCES SPECIFICALLY EXPRESSED IN MATURE T CELLS

(75) Inventors: David Klatzmann, Paris; Patrick Salmon, Veltra-Monthoux; Olivier Boyer, Paris, all of (FR)

(73) Assignee: Universite Pierre et Marie Curie, Paris (FR)

( * ) Notice: Subject to any disclaimer, the term of this patent is extended or adjusted under 35 U.S.C. 154(b) by 0 days.

(21) Appl. No.: 09/000,127

(22) PCT Filed: Jul. 17, 1996

(86) PCT No.: PCT/FR96/01122

§ 371 Date: Jan. 16, 1998

§ 102(e) Date: Jan. 16, 1998

(87) PCT Pub. No.: WO97/04118

PCT Pub. Date: Feb. 6, 1997

(30) Foreign Application Priority Data

Jul. 17, 1995 (EP) ................................................. 95/08616

(51) Int. Cl.[7] ............................ C12P 21/06; C12N 15/64; C12N 15/09; C12N 5/06; A61K 31/70

(52) U.S. Cl. .................... 435/69.1; 435/91.41; 435/456; 435/320.1; 435/372.3; 435/377; 514/44

(58) Field of Search ............................... 435/69.1, 91.41, 435/456, 320.1, 372.3, 377; 514/44

(56) References Cited

U.S. PATENT DOCUMENTS

| | | | |
|---|---|---|---|
| 5,843,432 | 12/1998 | Klatzmann et al. | 424/93.21 |
| 5,877,010 * | 3/1999 | Loeb | 435/320.1 |
| 5,948,675 | 9/1999 | Klatzmann et al. | 435/320.1 |
| 6,048,525 | 4/2000 | Klatzmann | 424/93.21 |

FOREIGN PATENT DOCUMENTS

WO 93/08844   5/1993   (WO).

OTHER PUBLICATIONS

Marshall, E. Gene therapy on trial. Science 288:951–957, May 2000.*

Fox, J.L. Investigation of gene therapy begins. Nature Biotech. 18:143–144, Feb. 2000.*

Anderson, W.F. Human gene therapy. Nature. 392(Suppl):25–30, Apr. 1998.*

Hanna et al., Molecular and Cellular Biology, Specific Expression of the Human CD4 Gene in Mature CDr$^+$CD8$^-$ and Immature CD4$^+$CD8$^+$T cells and in Macrophages of Transgenic Mice, Feb. 1994, pp. 1084–1094.

Killeen et al., The EMBO Journal, "Regulated expression of Human CD4 rescues helper T cell development in mice lacking expression of endogenous CD4", 1993, pp. 1547–1553.

Salmon et al., Proceedings of the National Academy of Sciences, "Characterizationof the human CD4 gene promoter: Transcription from the CD4 gene core promoter is tissue–specific and is activated by Ets proteins", Aug. 1993, pp. 7739–7743.

(List continued on next page.)

Primary Examiner—David Saunders
Assistant Examiner—Mary Beth Tung
(74) Attorney, Agent, or Firm—Venable; Michael A. Gollin

(57) ABSTRACT

The present invention relates to compositions and methods for the expression of nucleic acids or polypeptides into mature T lymphocytes. The invention relates more specifically to methods of selective gene expression into mature T lymphocytes, based on CD4-derived regulatory sequences, such as CD4-derived enhancer sequences. The invention is particularly suited for regulating gene expression into mature T lymphocytes in vitro, ex vivo or in vivo, upon genetic modification of hematopoietic precursors and maturation thereof.

10 Claims, 11 Drawing Sheets

OTHER PUBLICATIONS

Sawada et al., Molecular and Cellular Biology, "Identification and Characteristic of a T–Cell–Specific Enhancer Adjacent to the Murine CD4 Gene", Nov. 1991, pp. 5506–5515.

McCready P.M. et al., "Transient Transfection of T CellLines with the Murine CD4 Promoter and the T Cell–Specific Enhancer", Mar. 1994, pp. 4554.

Salmon et al., The Journal of Immunology, "Characterization of an Intronless CD4 Minigene Expressed in Mature CD4 and CD8 T Cells, but not Expressed in Immature Thymocytes", Mar. 1996, pp. 1873–1879.

* cited by examiner

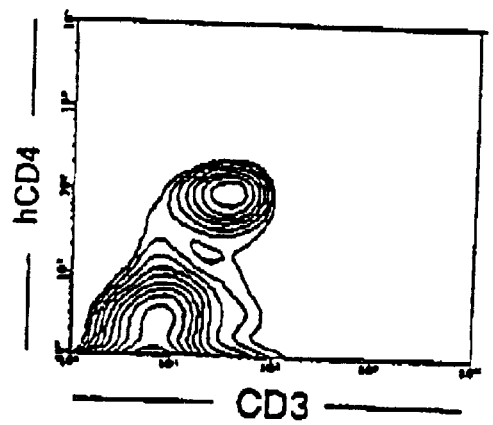
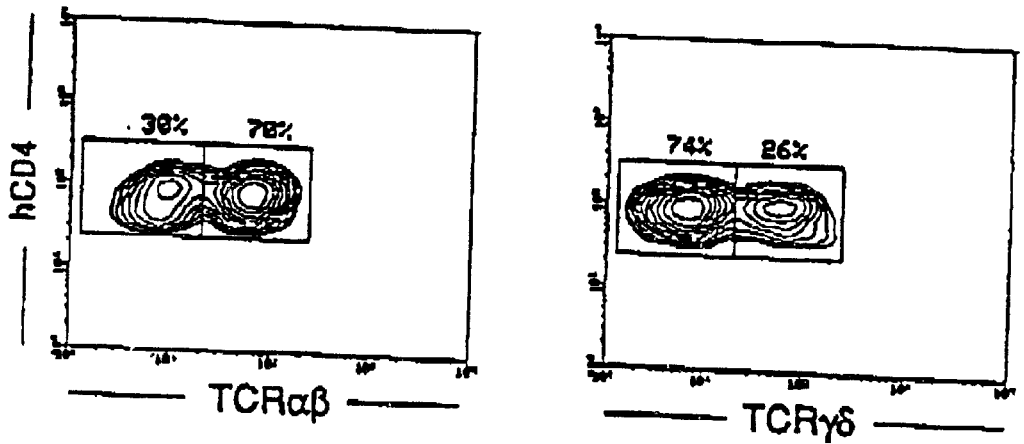
Fig. 4

```
CTGCAGCCTC AACTTCCTGG GCTCAAGCAA TCCTCCCACC TCGGCCTCCT AAAATACTGG
GATTATAGGC ATGAGCCACC ACTCCCAGCA CCACTTTTTT CAGACTGGAA AAGAACACTC
ACATGTGCAT CTTTAAATGA CACTTGGGCT GTGGTATGGA GAATGGCCAC CAGTGAGTAG
GCAGGAGCTG TTGTCCGAGC AAGGGCTGAT ATTGGCATCT TGGATTGGCA TGGTGGCAGT
AGTGGTAGTG CAGAGTGACT TGGGTAGATT TTGGAGCATT TAGAAGGTAC ATCCACAGGA
ACTGGTAAAT AAATACGTGG GAGAAGTTGG GTGAAGGGGG TGTCAAAGAT TACACCCAAT
TTATTTTGCT TGGGAAGTTG GTGGATGGTG AGCCCCTCAC TGAGTGAGAA GCCTGGAGAA
GCAGGTTTGG AGGGTGGTAG TATGCAGGTG GTATGCATAG TTGGGATGTG TGTTGAGTTT
GCTATGTCCG GTGAGCTTCC CAGTGGAGAT GTCCAATGGG CAGACGGATA CTCACATAGA
GAGTTCATGG TAGATTCGGG CTAGAGGAAA GCACCTGAGG CCTGGCCAGA GACGCCTAGA
GGAACAGAGC CTGGTTAACA GTCACTCCTG GTGTCTCAGA TATTCTCTGC TCAGCCCACG
CCCTCTCTTC CACACTGGGC CACCTATAAA GCCTCCACAG ATACCCCTGG GGCACCCACT
GGACACAATT GCCCTCAGGG CCCCAGAGCA AGGAGCTGTT TGTGGGCTTA CCACTGCTGT
TCCCATATGC CCCCAACTGC CTCCCACTTC TTTCCCCACA GCCTGGTCAG ACATGGCACT
ACCACTAATG GAATCTTTCT TGCCATCTTT CTTTTTCCCT TTAACAGTGG CAGTGACACT
TGACTCCTGA TTAAGCCTGA TTCTGCTTAA CTTTTCCCT TGACTTTGGC ATTTTCACTT
TGACATGTTC CCTGAGAGCC TGGGGGTGG GGAACCAGCT CCAGCTGGTG ACGTTTGGGG
CCGGCCCCAGG CCTAGGGTGT GGAGGAGCCT TGCCATCGGG CTTCCTGTCT CTCTTCATTT
AAGCACGACT CTGCAG
```

FIG. 6

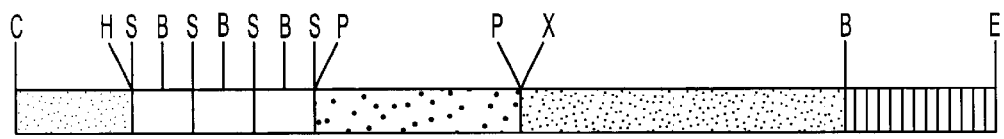
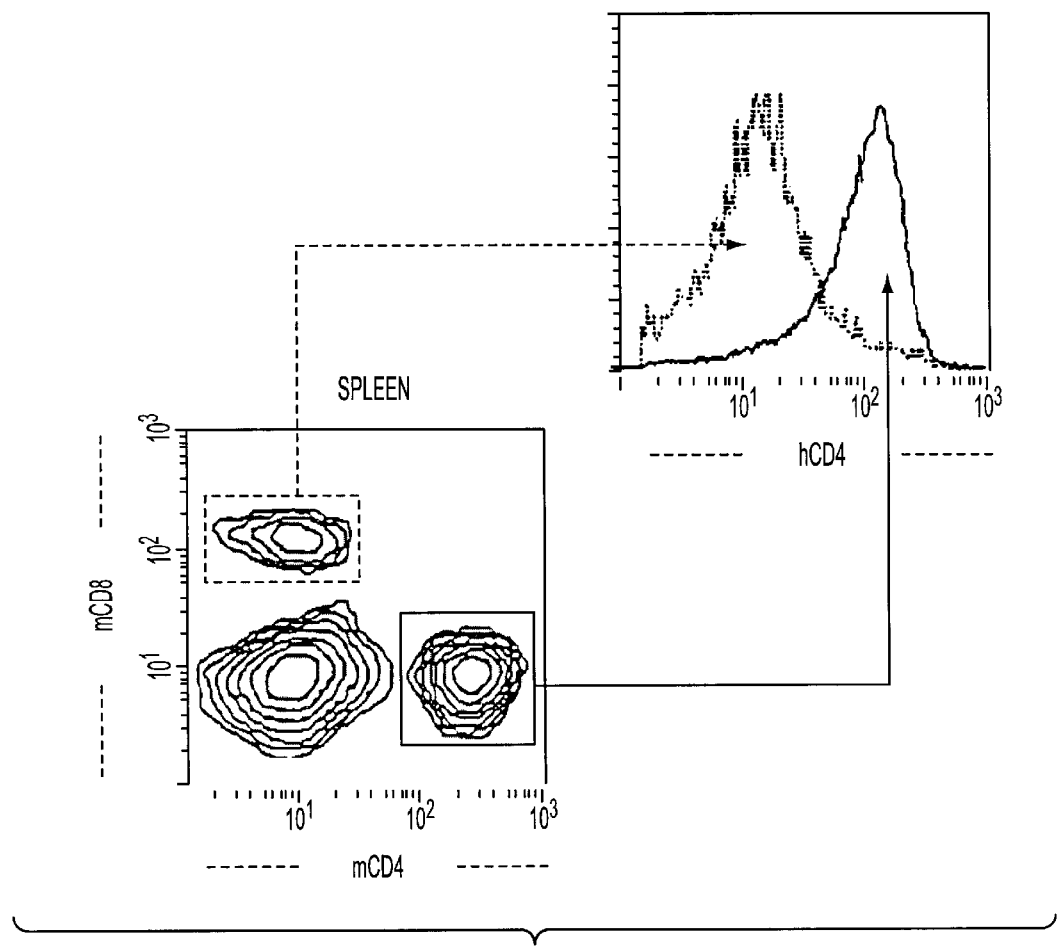
FIG. 7

CD4 GENE REGULATORY SEQUENCES SPECIFICALLY EXPRESSED IN MATURE T CELLS

FIELD OF THE INVENTION

The present invention relates to the use of regulatory sequences which are derived from the CD4 gene in vectors for expressing a heterologous gene or a transgene, with these sequences conferring on the vectors, when the latter are integrated into cells of the hematopoietic system, in particular stem cells, or, more generally, bone marrow cells, a specific expression within mature T lymphocytes, excluding immature T lymphocytes, in particular following repertoire selection.

BACKGROUND

During the maturation of T cells, expression of the CD4 and CD8 receptors responds to a complex mechanism of regulation; differential expression of the CD4 and CD8 glycoproteins is coupled to the choice of one of the pathways of differentiation either into helper T lymphocytes or into cytotoxic T lymphocytes; thus, thymocytes, that is the hematopoietic cells which are involved in a T differentiation pathway, first of all possess a CD4– CD8– phenotype (double negative or DN thymocytes); they then acquire joint expression of the CD4 molecule and the CD8 molecule, thereby forming double positive (DP) CD4+ CD8+ thymocytes and, finally, this population differentiates into single positive (SP) lymphocytes which express ether CD4, in the case of the helper T lymphocytes, or CD8, in the case of the cytotoxic T lymphocytes. Thymocytes which bind to class I histocompatibility molecules will become CD4+ CD8+ cytotoxic T lymphocytes while those which bind to class II molecules will become CD4+ CD8– helper T lymphocytes; after this intrathymic process of repertoire selection, the thyrnocytes leave the thymus and reach the peripheral system: i.e. blood and lymphoid organs.

This differentiation process is summarized in Nicolic-Zugic, J, (1991) Immuncol. Today 12: 65–70.

Many groups are currently studying the regulation of the expression of the CD4 gene since elucidation of the mechanism of this expression could contribute towards understanding the manner in which T cell development is controlled.

Several groups are working on the regulatory sequences of the human or murine CD4 gene. Those most recent studies which may be cited are the following: Killeen et al. (EMBO Journal Vol. 12 No. 4 p. 1547, 1993) demonstrated that a transgene carrying human CD4 of a size of approximately 35 kb possessed all the requisite genomic sequences for controlling expression during development in transgenic mice. Two distinct regulatory elements in this fragment were identified as being critical for expressing the transgene: the first is an enhancer sequence which is situated either 13 kb upstream of the cap site of the murine CD4 or 6 kb upstream of the human CD4. Blum M. D. et al. (J. Exp. Med. (1993) 177 No. 5: 1343–1358) identified and sequenced the human CD4 enhancer while Sawada et al. (Mol. Cell. Biol; 11 55: 5506–5515, 1991) identified and sequenced the murine CD4 enhancer. These two groups demonstrated that expression of this enhancer is specific for the CD4 gene in mature or immature T lymphocytes; P. Salmon et al. (Proc. Natl. Acad. Sci., USA 90: 7739–7743 (1993)) analyzed the structure and the sequence of the human CD4 promoter and compared it with that of the murine CD4 promoter. They identified a fragment of approximately 1100 base pairs which exhibits the function of a specific CD4 promoter. Aligning this sequence with that of the murine CD4 promoter indicates a very similar structure, as FIG. 1 of this latter paper shows.

Differentiation of the T lymphocytes employs other regulatory elements of the silencer type, whose presence leads to a decrease in, or cessation of, transcription of genes when they are in their vicinity. In Cell 77: 911–929, (1994), Sawada et al. demonstrated the existence of a silencer in an initial intron of the CD4 gene, one of the functions of which silencer is to extinguish transcription of the CD4 gene in mature CD8+ T lymphocytes.

Finally, the human CD4 gene was analyzed by Z. Hanna et al. (Mol. and Cell. Biology (1994) p. 1084–1094) in a construct which comprises at least 3 introns of a total length of 12 kb.

All the abovementioned recent studies indicate that expression of the CD4 cene is controlled in a similar manner in human and murine cells; nevertheless, the relationships between the different regulatory elements and their functions have not been elucidated.

SUMMARY OF THE INVENTION

The present invention results from the discovery, which was made by the inventors, of a combination of regulatory sequences which exhibit properties which are unexpected and entirely unforeseeable: this combination, which is composed of genetic elements which are derived from sequences which are located 5' of the CD4 gene, where appropriate combined with the cDNA of the CD4 gene, is expressed in a restricted manner in mature T cells and NK cells in a transgenic mouse model; it has not been possible to detect any expression in immature T cells, including double positive or double negative thymocytes. This group of regulatory sequences is the first to have this specificity of expression, something which is especially important, in particular for use in the context of gene therapy, for programs which would require a gene to be expressed specifically in mature T lymphocytes.

There was nothing in the state of the art to suggest that it was possible for such a combination to lead to this result.

The present invention results from the discovery that while the combination of the CD4 enhancer and promoter promotes expression of a reporter gene, in this case the cDNA of the human CD4 gene, in mature mouse thymocytes, this reporter gene is not expressed in immature CD4+ CD8+ double positive thymocytes; this result is surprising in that it implies the existence of an additional regulatory element which is as yet unknown and which would enable the CD4 gene to be expressed at the immature stage; this element, which is thought to act in "cis", is thought to be missing from the construct since no mouse regulatory element which would be able to act in trans is effective for bringing about such expression in the immature cells.

A foreseeable result is that linking the silencer described by Sawada et al. 1994 (see above) to this combination forms a cassette for expressing a heterologous gene exclusively in CD4+ CD8– SP helper T cells.

The present invention relates to a system for expressing a protein or a heterologous gene, which system comprises a recombinant vector which can be used for transducing cells of the hematopoietic line, in particular blood or marrow stein cells, in such a way that the cell which has been thus transduced will only express the protein or the heterologous gene which is carried by the vector in mature T cells after repertoire selection, to the exclusion of expression in immature T cells, in particular CD4– CD8– and CD4+ CD8+ cells; said vector of the expression system is provided with all the sequences which are required for its expression and it is characterized in that it contains at least one enhancer of a CD4 gene which is derived from the same species or from a different species.

The vector of the expression system may also contain, combined with the enhancer, a promoter which consists of one of the following sequences:

the promoter of the human CD4 gene, as depicted in FIG. 6, or the sequence contained between nucleotides –496 and +16 in the P. SALMON (1993, see above) numeration (FIG. 6), or the sequence contained between nucleotides –165 and +16 (P. SALMON, 1993, see above) (FIG. 6), or any sequence which is derived from one of the preceding sequences by means of the addition, deletion or substitution of nucleotides without substantial modification of the expression of the heterologous protein under the control of this promoter.

A specific example of an efficient enhancer, within the context of this invention, is that of murine CD4, which enhancer consists of 339, or all or part of the 339 base pairs and is described in the abovementioned Sawada et al. (1991), with it being possible for this enhancer to be present either in the form of a single sequence or in the form of a sequence which is repeated from two to five times, and with the sequence of this enhancer being the following (SEQ ID NO: 1:)

```
TGTTGGGGTT CAAATTTGAG CCCCAGCTGT TAGCCCTCTG

CAAAGAAAAA AAAAAAAAAA AAAGAACAAA GGGCCTAGAT

TTCCCTTCTG AGCCCCACCC TAAGATGAAG CCTCTTCTTT

CAAGGGAGTG GGGTTGGGGT GGAGGCGGAT CCTGTCAGCT

TTGCTCTCTC TGTGGCTGGC AGTTTCTCCA AAGGGTAACA

GGTGTCAGCT GGCTGAGCCT AGGCTGAACC CTGAGACATG

CATCCTCTGT CTTCTCATGG CTGGAGGCAG CCTTTGTAAG

TCACAGAAAG TAGCTGAGGG GCTCTGGAAA AAAGACAGCC

AGGGTGGAGG TAGATTGGT
```

The human CD4 enhancer described by M. D. Blum et al. (cited above) comes within the area of the invention, whether it is used alone or in combination with the CD4 promoter.

The term enhancer of a CD4 gene is understood as being not only the sequences described by Sawada et al. or by Blum et al. but also other sequences which are derived from other mammalian species and which exhibit a sufficient degree of homology with the above sequences, with these other sequences in particular including, for example, the specific CD4-1, CD4-2 and CD4-3 nuclear protein sequences described in Sawada et al. (1991).

The implication of this specific property—i.e. non-expression in immature T cells and expression in mature T cells—reveals the advantages of incorporating the construct of the invention into medicaments which can be used in gene therapy for all the indications where transgene expression in T cells could be a means of treating or preventing certain pathologies or dysfunctions, in particular viral infections, particularly infections due to HIV, pathologies in the expression of certain genes in the T lymphocytes, for example deficiency in adenosine deaminase or, more generally, primary or secondary immune deficiencies, autoimmune pathologies or grafts. However, the therapist comes up against the following difficulty: if mature T lymphocytes are taken as the targets for gene therapy, he is obliged to transfer genes into these mature T lymphocytes ex vivo and these latter lymphocytes have to be previously cultured in order to effect this transfer using the appropriate vectors; after reinjection, the half-life of the T lymphocytes is relatively short; by contrast, if the strategy selected is to target the hematopoietic stem cells which give rise, after differentiation, to the T lymphocytes, two different problems are then met with: the first is that of an expression of the gene of interest in the stem cells which is not always desirable, and the second is that of the possible disruption of repertoire selection in the thymus which is induced by expression of the heterologous gene in immature cells.

The construct of the invention enables this double drawback to be overcome by means of transferring, to the hematopoietic stem cells, a heterologous gene which will only be expressed after the repertoire selection has taken place.

As has been mentioned above, the transfer of genes into hematopoietic cells has been envisaged for expressing a protein of interest of the adenosine deaminase type in mature T lymphocytes for which the current treatment is transduction of cultured T lymphocytes, which have been harvested by means of leucopheresis, with a recombinant retroviral vector (for a summary of these experiments, see Anderson W. F. Human Gene Therapy, Science (1992), 256: 803–814).

Serious viral infections (AIDS) or the prevention of immune stimulation of the autoimmune disease or GVHD (graft-versus-host disease) type represent another type of application of the transfer of genes into hematopoietic cells. The approach consists in booby-trapping T lymphocytes by incorporating into them a transgene which consists of a suicide gene, for example HSV1 thymidine kinase (HSV1-TK) or a functional equivalent of this gene whose expression product is able to metabolize, in situ, a pharmaceutically inactive substance into a toxic derivative for specifically inducing the destruction of these cells, with an example of such a derivative in the case of HSV1-TK being ganciclovir.

Obtaining expression vectors which possess the specific expression qualities of the vectors of the invention makes it possible to overcome the abovementioned drawbacks of the transfers into stem cells or into mature cells.

The vectors which can be used for transferring genes into hematopoietic stem cells (HSCs), and which are able to incorporate the regulatory elements of the invention which enable the foreign gene to be specifically expressed exclusively in mature cells, may be selected from any of the vectors which are suitable for transfecting these HSCs. These vectors are essentially viral vectors of the adenovirus or adenoassociated virus (AAV) type or retroviral vectors, or else non-biological systems for delivering nucleic acid in vivo. A summary of the essential characteristics of these different types of vector will be found in "Thérapie génique (Gene therapy), Edition John Libbey, (1993) pages 3 to 33".

Specific retroviral vectors have been described for booby-trapping T cells either with regard to infection with retroviruses or in order to induce GVHD tolerance and are described in U.S. Pat. Nos. 6,048,525 , 5,843,432 and U.S. Pat. No. 5,948,675, and patent application No. WO93/08844 the contents of which patent applications are incorporated into the present application by reference.

In the expression system of the invention, whose expression vector contains a cassette which consists of the above-described promoter or enhancer/promoter combination, the heterologous protein which is capable of being expressed in mature T lymphocytes can be selected as a protein which exhibits a toxicity which is dependent on the presence of a substance: thus the heterologous protein can advantageously be HSV1-TK thymidine kinase or a protein which is derived from this thymidine kinase as long as it retains the functional characteristics of a kinase; while the substance can be a nucleoside analog such as acyclovir or ganciclovir, which is capable, after having been phosphorylated by the thymidine kinase, of being incorporated into dividing DNA and of bringing about the death of the mature T lymphocyte.

Examples of constructs which enable this "suicide gene" approach to be implemented in CD4+ T lymphocytes by means of transfecting an HSV1-TK gene and treating with ganciclovir have been described in Caruso M. and Klatzmann D. (Proc. Natl. Acad. Sciences (1992) 89: 182–186).

The present invention also relates to cells of the hematopoietic cell line, in particular HSCs which are transfected with an expression vector which consists at least of a sequence encoding a heterologous protein, a promoter and a polyadenylation sequence, which cells are characterized in that the said vector contains at least one enhancer sequence from a mammalian CD4 gene of the same species or of a different species, where appropriate in combination with a CD4 gene promoter, with the heterologous protein being principally expressed in mature T lymphocytes which are derived from repertoire selection.

Preferably, the promoter consists of one of the above-described sequences, and consists, or is derived from, the human CD4 gene promoter as depicted in FIG. 6.

The promoter can also be a cytokine promoter or the promoter of a cytokine receptor such as that of interleukin 2.

In the expression systems of the invention, the expression vector contains, upstream or downstream of the sequence to be expressed, a murine CD4 enhancer which consists of the 339 base pair sequence described in Sawada et al. (1991). One embodiment is to include between 1 and 5 copies of this enhancer or of a derived enhancer as defined above, preferably 3 copies.

The cells which are transfected with a recombinant vector expressing a protein which exhibits conditional toxicity for mature T cells also form part of the invention; in particular, cells which are transfected with a vector carrying HSV1-TK thymidine kinase or a protein which is derived from this kinase forms part of the invention. The thymidine kinase gene can then be dependent on a promoter such as described above or on a specific promoter, in particular the interleukin 2 promoter, which is combined in any manner with an enhancer as described above. It should be recalled at this point that activation in the case of T lymphocytes is associated with cell division; since the ganciclovir is only toxic for cells which are dividing and expressing HSV1-TK, it is not, therefore, necessary to be able to control expression of the HSV1-TK gene extremely strictly during cell activation. An expression which is restricted to mature T lymphocytes is adequate; thus, even if a quiescent mature T lymphocyte expresses the HSV1-TK protein constitutively, this lymphocyte will not be destroyed, even in the presence of ganciclovir. By contrast, as soon as the cell has been activated and is dividing, the ganciclovir triphosphate will already be present in the cell and will make it possible to eliminate the cell immediately.

The therapeutic strategy which consists in carrying out a bone marrow graft using cells which harbor an HSV1-TK transgene under the control of the regulatory sequences of the invention will then afford the requisite security of the gene not being expressed during the whole of the T lymphocyte differentiation process and therefore of not disrupting repertoire selection and of not risking the possibility of killing cells which are in permanent division, as the immature thymocytes are. Finally, it is a sought-after aim that the TK gene should be expressed permanently by all the T lymphocytes. If a graft-versus-host reaction appears when bone marrow stem cells which are transduced with TK are reinjected into a patient, with the graft-versus-host reaction involving activation of certain T lymphocytes of the graft which recognize histocompatibility antigens of the recipient, the TK system should make it possible to eliminate these lymphocytes by treating the patient with ganciclovir or acyclovir.

The present invention also relates to the use of specific regulatory sequences of the CD4 gene, in particular the enhancer, or the combination of the enhancer and a promoter, as described above, in the production of a medicament which can be used in gene therapy for specifically destroying activated T lymphocytes, with these regulatory elements being integrated into an expression system which is capable of transforming the cells of the hermatopoietic system; such a use makes it possible to envisage specifically expressing the transgene, which has been incorporated into the vector, within mature CD4+ CD8– and CD4– CD8+ T cells, with this expression being totally repressed during the entire differentiation process up to and including repertoire selection in the thymus.

We recalled above that Sawada et al. demonstrated, in Cell (1991), the existence of a transcriptional silencer which is specific for the CD4 gene and which is located in the first intron of the gene. The combination, which has thus been characterized, of the silencer and the regulatory sequences of the invention, whether they be the enhancer alone or the enhancer combined with a promoter, with enhancer and promoter retaining the above definitions, form part of the invention as does their use in the production of a medicament which can be used in gene therapy for transforming the stem cells of the hematopoietic system. Such a combination of regulatory elements in a vector for expressing a heterologous protein makes it possible to envisage expressing this heterologous protein exclusively in mature CD4+ CD8– T lymphocytes, excluding immature T lymphocytes and CD8+ cytotoxic T lymphocytes.

The use of an expression system which comprises vectors which are provided with the regulatory sequences of the invention is particularly recommended in the production of a gene therapy medicament for preventing or treating graft rejections or graft-versus-host reactions or for treating autoimmune diseases; it can also be taken into consideration for preparing a medicament which can be used for preventing or treating infections due to viruses, in particular due to HIV. The use of the construct which additionally comprises a silencer can make it possible to prepare medicaments for gene therapy.

Thus, the findings which are currently available suggest that the combination enhancer/promoter/silencer of the CD4 gene should be sufficient to obtain expression in all CD4+ cells (including DP cells). However, as reported in this invention, it appears that the enhancer/promoter combination clearly has an innovative character since it brings about expression which is restricted to mature T cells; while the absence of the silencer only has an effect on expression in CD8+ cells, it is not linked to the stage of development.

The examples below illustrate the unexpected characteristics of the combination of regulatory elements of the invention and the properties which it confers on the cells into which the elements have been integrated.

On the basis of the findings which are described in this document, the skilled person will very readily know how then to adapt the construct which should be employed for a specific prophylaxis or therapy which he might wish to implement and which requires specific expression in mature CD4+ CD8− and CD4− CD8+ T cells or exclusively in mature CD4+ CD8− T cells.

BRIEF DESCRIPTION OF THE DRAWINGS

In the examples which follow, the figures have the following legends:

In FIGS. 1A and 1B, the letters indicate restriction sites and have the following meanings: H=Hind3, S=Sph1, P=Pst1, X=Xba1, B=BamH1, E=EcoR1.

The numbers represent the percentage of hCD4+ thymocytes in each subpopulation for the two experiments which are depicted in this figure. Each result was reproduced seven (line 7) and thirteen (line 10) times in independent experiments.

FIG. 4 depicts an analysis of the expression of CD3, TCR αβ and TCR γδ in DN thymocytes which are expressing hCD4. The transgenic mouse thymocytes were labeled with a QR-coupled anti-hCD4 monoclonal antibody, a mixture of PE-coupled anti-mCD4 and anti-mCD8 antibodies and either (A) an FITC-coupled anti-TCR αβ antibody or an FITC-coupled anti-TCR γδ antibody. The phenotypes of the DN thymocytes (A) and the DN thymocytes expressing hCD4 (B) were studied by making windows on the PE− cells and QR+PE− cells, respectively. The results depicted in this figure are representative of five (line 10) and one (line 7) reproducible experiments.

Figure 5:
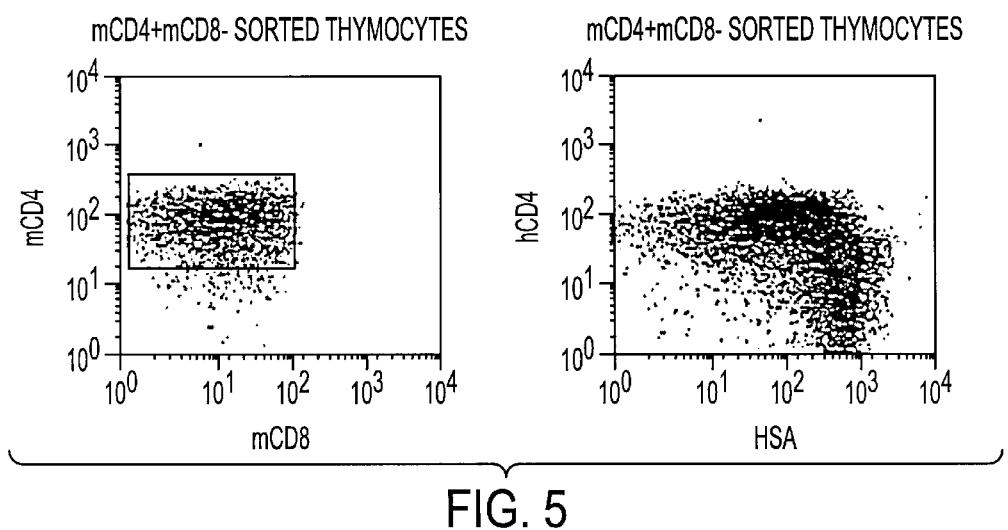

FIG. 5 depicts an analysis of the expression of hCD4 and HSA on SP CD4 thymocytes. The SP CD4 thymocytes were isolated by cell-sorting and washed; they were then subjected to a second immunolabeling with PE-coupled anti-HSA and QR-coupled anti-hCD4 monoclonal antibodies. The experiment which is depicted was reproduced three (line 10) and one (line 7) times in independent experiments.

FIG. 6 (SEQ ID NO:2) depicts the sequence of the promoter of the gene encoding human CD4 and is taken from P. Salmon et al. (Proc. Natl. Acad. Sci., USA 90: 7739–7743 (1993)).

FIG. 7 depicts the characterization of the human CD4 gene silencer (Sil) which makes it possible to express a transgene differentially in mature CD4+ T lymphocytes and not in mature CD8+ lymphocytes.

Figure 8A:
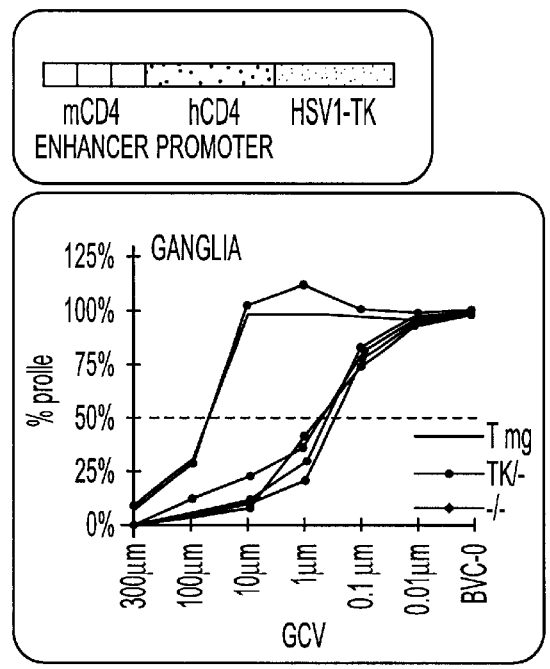
Figure 8B:
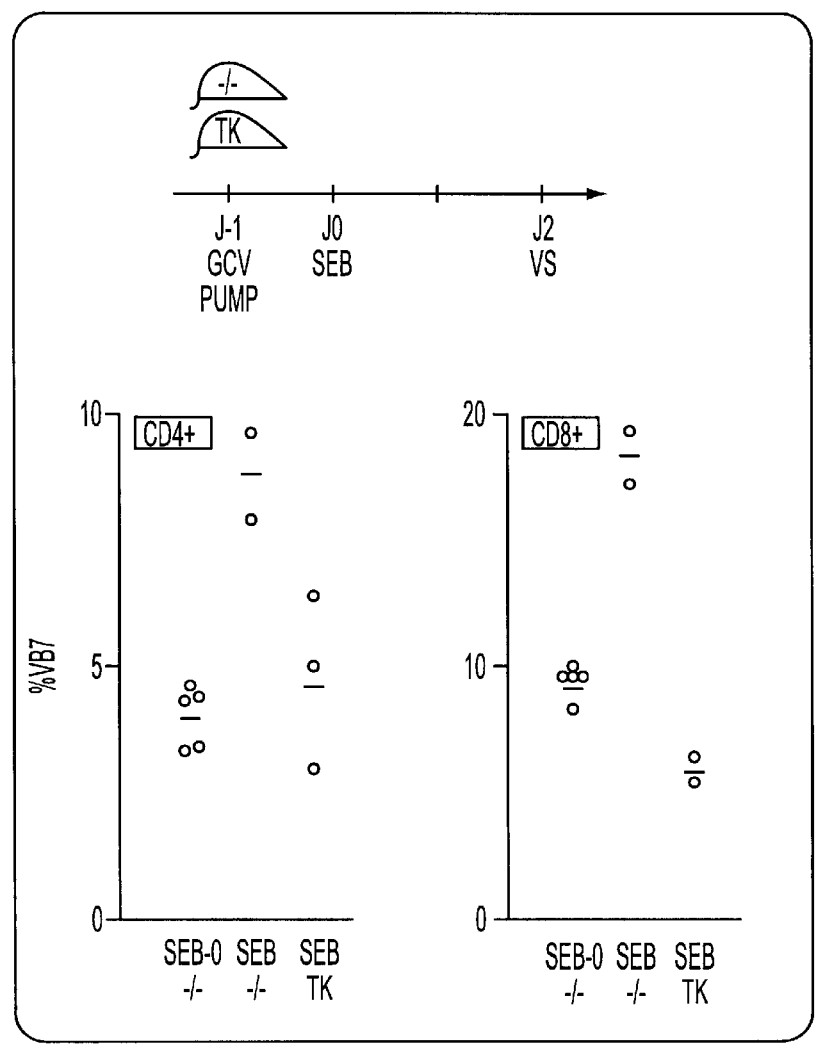

FIG. 8 depicts the specific depletion, by ganciclovir, of CD4+ and CD8+ T lymphocytes (FIG. 8a) in response to a mitogen (ConA) in vitro and (FIG. 8b) the in-vivo depletion of T lymphocytes expressing TCR Vβ7 in response to stimulation with the superantigen SEB.

Figure 9:
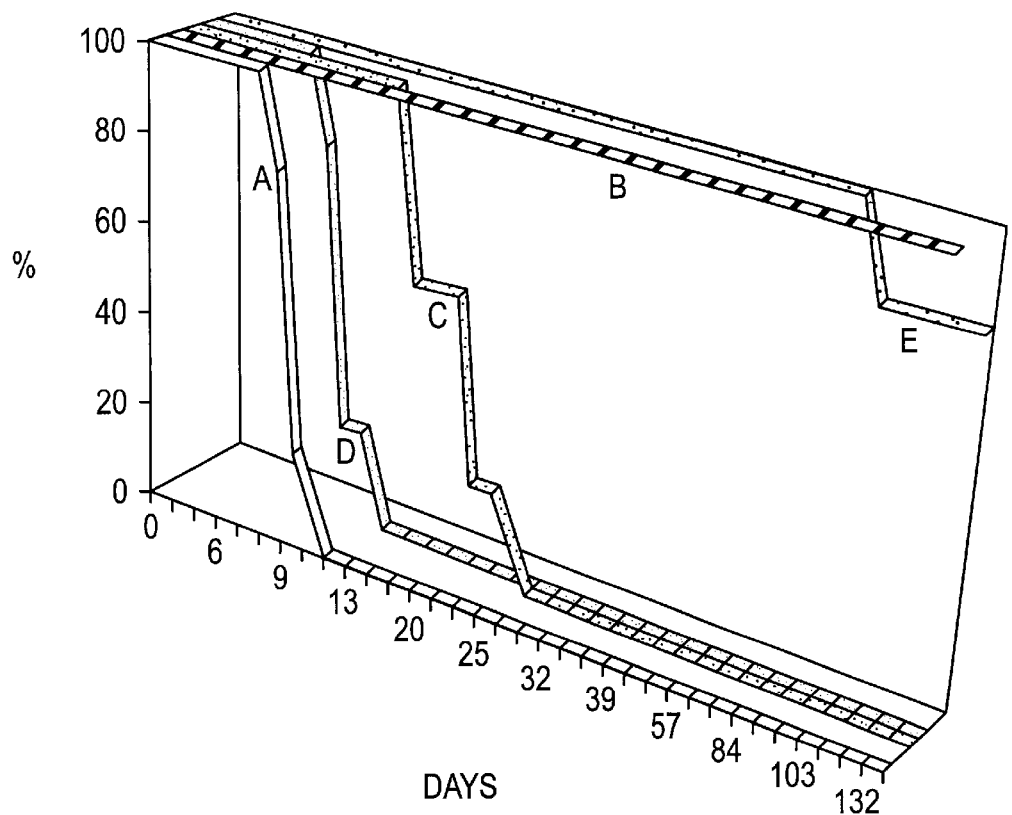

FIG. 9 shows the results of an analysis of irradiated mice which are given a bone marrow graft which is or is not accompanied by splenocytes which are derived either from transgenic mice or from normal mice. The control mice, which are not grafted (BMG−) die as a consequence of the irradiation. The animals which are grafted with bone marrow alone, without splenocytes (BMG+), survive due to the bone marrow graft and there is no GVH as is the usual case in mice. The animals which are given a bone marrow graft and allogenic splenocytes which are derived either from transgenic mice which are treated with PBS (GVH/PBS) or from non-transgenic mice which are treated with ganciclovir (GVH/GCV NTG) die equally rapidly and exhibit all the clinical and histological signs of a GVH. Only the mice which have been given the bone marrow and splenocytes from transgenic mice which have been treated with ganciclovir (GVH/GCV) survive in the same way as the mice given the marrow graft, without any histological or clinical signs of GVH. The BMG− group is represented by curve A. The BMG+ group is represented by curve B. The GVH/GCVNTG group is represented by curve C. The GVH/PBS group is represented by curve D and the GVH/GCV group is represented by curve E.

Figure 10:
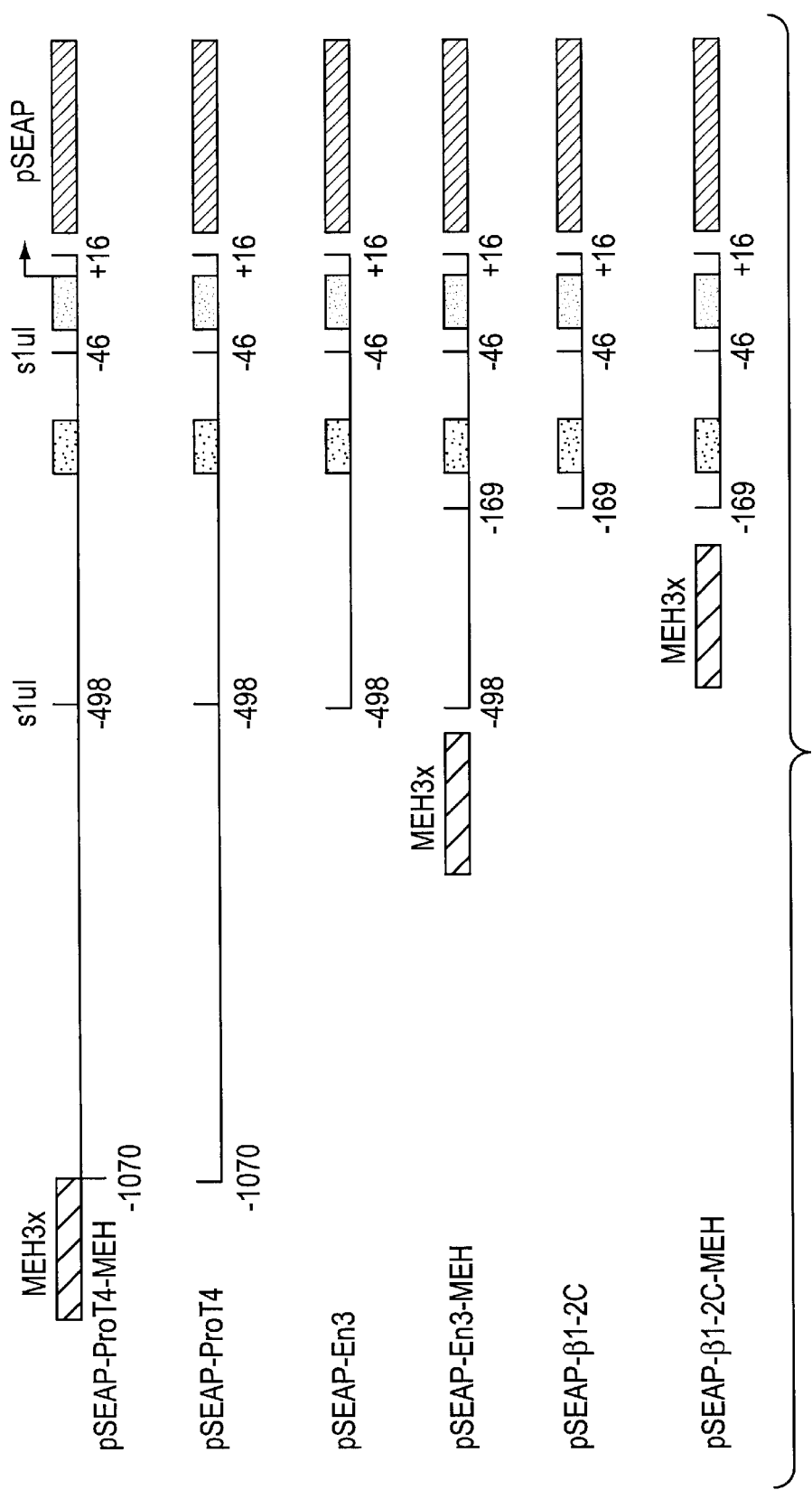

FIG. 10 depicts the characterization of the minimum sequences, derived from the regulatory sequences of the human CD4 gene, which are required for expressing a transgene. The transcription initiation site of the human CD4 gene is represented by a black arrow. The (reporter) gene for secreted human alkaline phosphatase is embodied by the acronym pSEAP. The black and gray-tinted rectangles represent the conserved 2 "box" and 3 "box" mouse-homologous sequences, respectively. Finally, "MEH3X" corresponds to the murine CD4 gene enhancer which, in the present test, is repeated three times.

Figure 11:
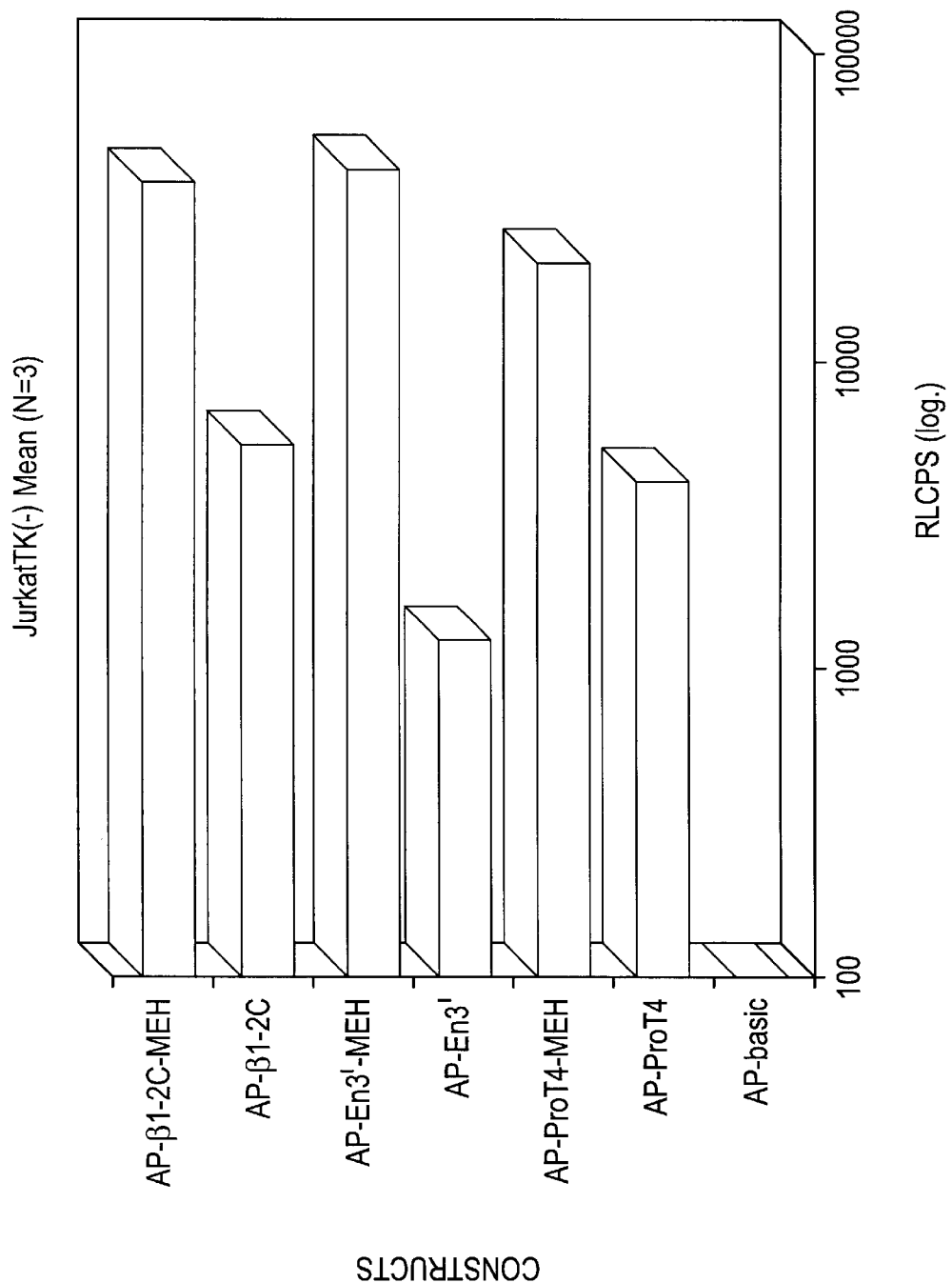

FIG. 11 depicts expression of the reporter gene following transfection of the different gene constructs of line 4 into Jurkat cells.

DETAILED DESCRIPTION

EXAMPLE 1

Figure 1A:
FIG. 1A depicts the pCD4 cassette, which consists of the 1100 base pair hCD4 promoter, the human CD4 cDNA, which is used here as a reporter gene, and the SV40 virus polyadenylation sequence.
Figure 1B:
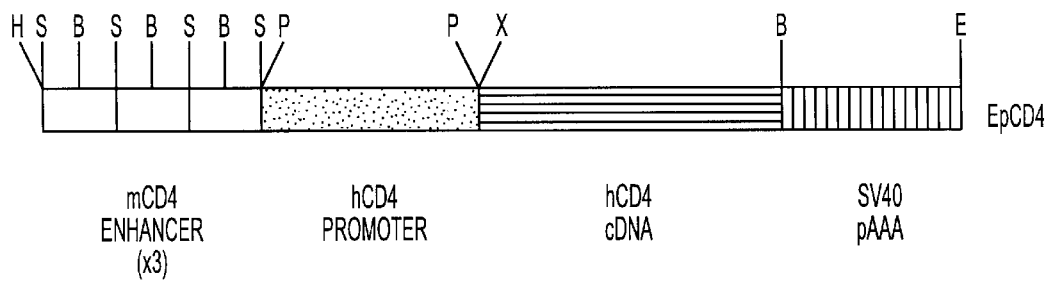
FIG. 1B depicts the EpCD4 cassette, which consists of the same elements as in the case of pCD4, which elements are provided upstream with 3 copies of the 339 base pair sequence of the mouse CD4 enhancer.

Expression of a Human CD4 Minigene in the Mature T Cells of Transgenic Mice:

Two plasmids were constructed:

the plasmid pCD4, which carries a 1100 base pair sequence corresponding to the human CD4 promoter and, downstream of that, the human CD4 cDNA and an SV40 polyadenylation sequence (FIG. 1A), the plasmid EpCD4, which is the same construct but which additionally comprises three repeats of the 339 base pair murine CD4 enhancer described in Sawada (1991) (FIG. 1B).

The CD4 cDNA is included in these constructs as a reporter gene, that is whose expression or non-expression in the transgenic mouse system is observed, with the expression being easy to detect by means of the flow cytometry techniques employed.

1—Materials and Methods

1a—Construction of the Transgenes

In order to construct pCD4, depicted in FIG. 1A, the Pst1 fragment of the human CD4 (hCD4) promoter described by P. Salmon et al. (1993) and comprising nucleotides −1076 to +20, was ligated to the 1.8 kb EcoR1-BamH1 cDNA fragment encoding the human CD4 protein; this protein has been characterized by Maddon P. J. et al. in Cell 42: 93:104 (1985). The polyadenylation sequence is derived from an 0.8 kb BamH1-Bgl2 fragment from the SV40 virus.

In constructing plasmid EpCD4 (FIG. 1B), a PCR-amplified fragment of the murine CD4 enhancer was added to the pCD4 construct directly upstream of the hCD4 promoter. Briefly, murine genomic DNA was subjected to PCR amplification using primers which were complementary to the flanking sequences of the 339 base pair minimum sequence of the above-described enhancer, which sequence contains additional Sph1 restriction sites. The PCR products were cloned into plasmid pCD4 and the sequences of the inserts were verified. A clone containing 3 copies of the murine enhancer was retained for constructing transgenic mice.

1b—Generation and Screening of the Transgenic Mice

Hind3-EcoR1 DNA fragments were generated from plasmids pCD4 and EpCD4 and separated by means of agarose gel electrophoresis. The transgenes were then eluted using the BIOTRAP™ elution system (Schleicher and Schuell, Dassel, Germany) and adjusted to a concentration of 5 ng/μl in 10 mM Tris-HCl, pH 7.4, 0.1 mM EDTA.

Transgenic mice harboring plasmids pCD4 and EpCD4 were obtained and characterized as described by Hogan B. et al. (1986) in Manipulating the Mouse Embryo, a Laboratory Manual; Cold Spring Harbour Laboratory Press, Cold Spring Harbour, N.Y. The transgenes were microinjected into the pronuclei of F2 zygotes which were obtained by crossing two: [C57 B1/6 DBA/2] F1s. The transgenic animals were detected by hybridizing DNA prepared from tail biopsies with a radiolabeled probe which is specific for human CD4 and which is the 1.8 kb EcoR1-BamH1 fragment of human CD4 and is described in the article by Maddon P. et al. (1985).

1c—Antibodies Employed

The following directly labeled monoclonal antibodies were employed, with the initials having the following meanings: FITC=fluorescein isothiocyanate, PE: phycoerythrin; QR: quantum red; SA: streptavidin; APC: allophycocyanin; PerCP: peridinine chlorophyll protein; m: murine; h: human.

List of the antibodies:
anti-mCD4 (rat IgG2b labeled with PFE or APC, clone YTS 191.1),
anti-mCD8 (rat IgG2b labeled with FITC or PE, clone YTS 169.4),
anti-mCD3 (hamster IgG labeled with FITC, clone 500-A2),
anti-mB220 (rat IgG2a labeled with FITC, clone RA3-6B2),
anti-mTCRαβ (hamster IgG labeled with FITC, clone H57-597) and
anti-mMAC1 (rat IgG2b labeled with FITC, clone M1-70.15),
obtained from Caltag Laboratories (San Francisco, Calif.);
anti-mTCRγδ (hamster IgG labeled with PE, clone GL3),
anti-mNK (mouse IgG2a labeled with PE, clones PK 136 and 5E6),
anti-mHSA (rat IgG2b labeled with PE, clone M1/69) obtained from PharMingen (San Diego, Calif.);
anti-hCD4 (mouse IgG1 labeled with QR, clone Q4120) and a negative control (mouse IgG1 labeled with QR, MPOC-21) obtained from Sigma Immunochemicals (St. Louis, Mo.)

1d—Preparation of the Cells and Analysis by Flow Cytometry

All the analyses were carried out on mice of from 8 to 20 weeks of age. The thymus, the spleen and the lymphatic ganglia are disrupted in DMEM (Dulbecco's modified Eagle medium) obtained from Life Technologies Inc. (Gaithersburg, Md.), resuspended with a pipette, centrifuged at 1100 rpm for 5 minutes and then resuspended in a labeling buffer consisting of PBS containing 2% fetal calf serum and 0.02% sodium azide. The suspension of splenic cells was mixed with two volumes of 0.8% ammonium chloride in order to lyse the erythrocytes and was then immediately centrifuged and resuspended in the labeling buffer. After counting, all the cells in suspension are adjusted to a final concentration of from 10 to 20×10⁶ cells/ml. For analyzing the B cells and the macrophages, a final concentration of 2% autologous serum was added to the coloration buffer before adding the monoclonal antibodies. The labelings were carried out by incubating from 1 to 2×10⁶ cells with the monoclonal antibodies at 4° C. for 30 minutes; after a final wash, the cells were fixed in from 0.5 to 1 ml of 1% paraformaldehyde in PBS. From 10 to 40,000 cells were analyzed by flow cytometry (FACSCAN™, Becton Dickinson, San Jose, Calif.) in this way.

Purified SP CD4+ CD8− thymocytes were obtained after subjecting a total thymus cell suspension to double color-labeling with APC-labeled anti-mCD4 antibodies and PE-labeled anti-mCD8 antibodies for 1 hour in ice and were then washed and filtered through a FALCON 2350™ (Becton Dickinson, Franklin Lakes, N.J.) nylon cell filter. The APC+ and PE− cells are sorted, in PBS buffer containing 0.02% sodium azide, using a FACSTARPLUS™ (Becton Dickinson).

When $10^6$ SP CD4+ CD8− cells have been obtained by cell-sorting, they are washed and resuspended in 250 μl of labeling buffer; they are then separated into two tubes and subjected to labeling with PE-labeled anti-HSA antibodies and either QR-labeled anti-hCD4 antibodies or with isotype control antibodies. The cells were analyzed on a FACSCAN™ as described above.

2—Results

2-1 Detectable Expression of the CD4 cDNA Reporter Gene in Vivo Requires the Presence of the Enhancer in Addition to the CD4 Promoter.

Table 1 below summarizes the percentage of cells expressing the hCD4 reporter gene in the thymus, the spleen, the lymphatic ganglia and the PBMNCs (peripheral blood mononuclear cells); the presence of the CD4 was analyzed by means of flow cytometry as described above. The figures in brackets indicate the number of animals tested, while the results are the means obtained for the different animals tested plus or minus the standard deviation.

TABLE 1

| Construct | Thymus | Spleen | Lymphatic ganglia | PBMNCs |
|---|---|---|---|---|
| pCD4 (7 cell lines) | <1 | <1 | N.D. | <1 |
| EpCD4 | 8 ± 3.0 (10) | 30 ± 6.1 (10) | 75 ± 13.4 (6) | 58 ± 14.0 (6) |

Seven transgenic lines were obtained which harbored from 1 to 40 copies of the pCD4 plasmid, which latter did not, therefore, include the enhancer; it was not possible to detect any hCD4-positive cell under these conditions.

In the case of the EpCD4 construct, four lines were obtained harboring from 5 to 20 copies of the construct, all of which lines express the hCD4 transgene; two of the lines were analyzed in detail (line 7 and line 10). The results for EpCD4 which are hown in the table were obtained with line 10, while similar results were obtained with line 7.

The cells of the spleen, the lymphatic ganglia and the PBMNCs are mature cells obtained after repertoire selection; this explains the markedly greater percentage of cells expressing CD4 in these categories as compared with the percentage obtained for the thymus.

In conclusion, it appears that the presence of the CD4 gene enhancer is necessary and sufficient for obtaining expression of the reporter gene.

2.2—Expression of the EpCD4 Transgene in Peripheral Lymphoid Organs.

The transgenic EpCD4 Lines 10 and 7 were analyzed in order to determine the cell types expressing the transgene. Thus, we carried out flow cytometry analyses after doubly or triply labeling splenocytes using monoclonal antibodies against human CD4 in combination with monoclonal antibodies which recognized different hematopoietic cell types.

Figure 2:
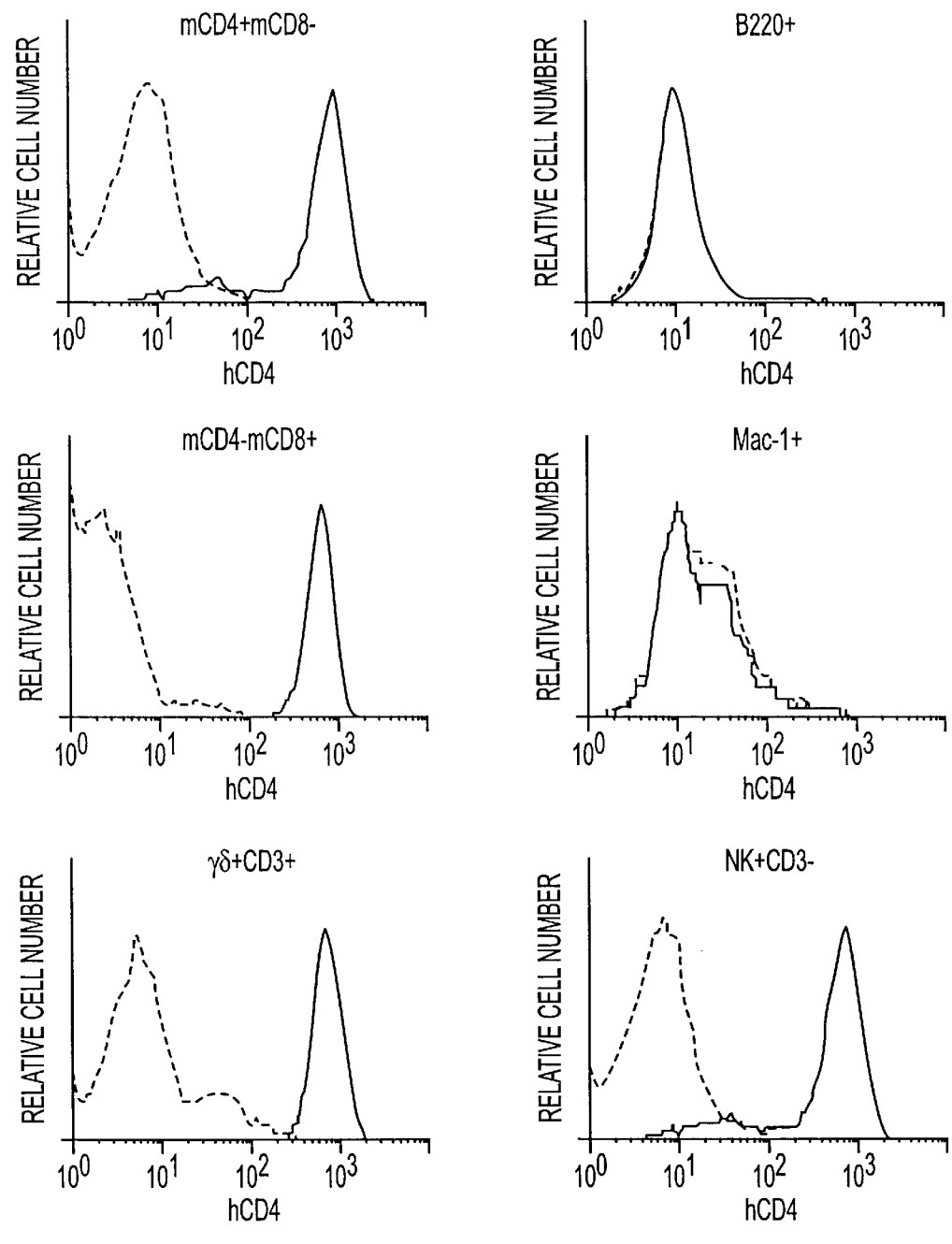
FIG. 2 depicts the expression of the hCD4 reporter gene at the surface of mononuclear cells from transgenic mouse spleen, i.e. SP CD4+, SP CD8+, γδ lymphocytes, B lymphocytes, macrophages and NK cells, respectively.

As FIG. 2 shows, the expression of hCD4 is restricted to T lymphocytes and to NK cells. Expression of hCD4 was detected in all the T cells at the same level as the cells express CD4 or CD8. Comparable expression is obtained in lymphocyte cells expressing a γδ receptor. It was not possible to detect any expression in either the monocytes or the B lymphocytes of the mice which were analyzed (FIGS. 2D–E).

The majority of the NK cells, defined as being recognized by both the PK136 and 5E6 monoclonal antibodies, were also found to express hCD4 to variable extents (FIG. 2F). Taken as a whole, these results show that expression of the EpCD4 transgene in peripheral cells is restricted to T cells and to NK cells.

The results shown in this figure were reproduced from three to twelve times in independent experiments. Two different monoclonal antibodies (PK136 and 5E6) were used in the analysis of the NK cells, with these antibodies revealing a proportion of hCD4+ cells of from 74 to 100%. These frequencies are always slightly higher in the 5E6+ cells than in the PK136+ cells.

The results which were obtained for the SP CD4+ and SP CD8+ lymphocytes were duplicated in the case of the lymphatic ganglia and the peripheral blood mononuclear cells.

While these results were obtained with line 10, comparable results were obtained with line 7.

3—Expression of the EpCD4 Transgene in Thymocytes.

Figure 3:
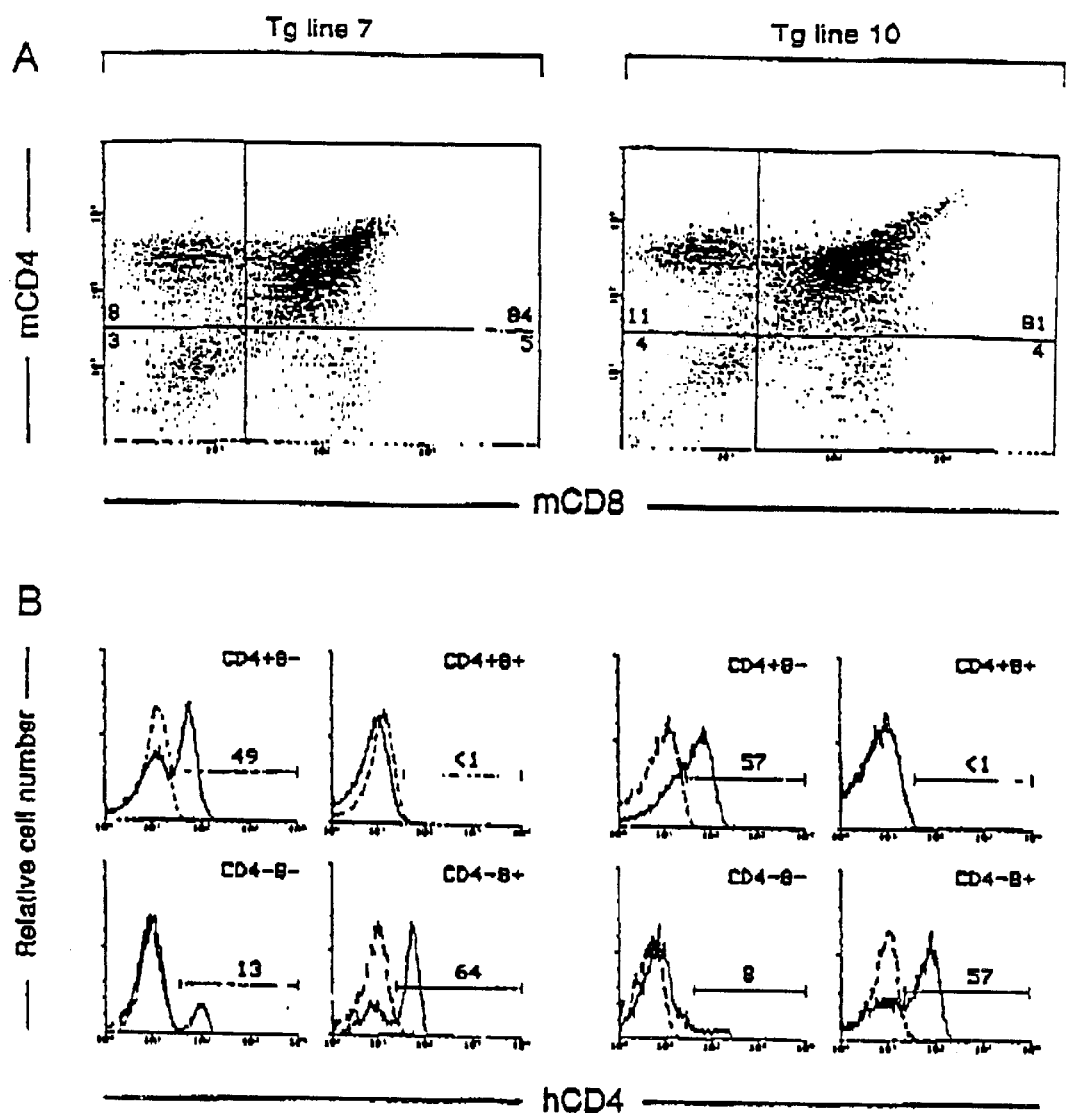
FIG. 3 depicts an analysis of the expression of the hCD4 reporter gene in transgenic mouse thymocytes by means of triple immunolabeling and flow cytometry. (A) shows the distribution of the thymocyte subpopulations which are defined by the expression of mCD4 and mCD8. The numbers in each field represent the percentage of each subpopulation in the thymus. (B) shows hCD4 expression in DN (CD4− CD8−); DP (CD4− CD8+); SP (CD4+ CD8−) and SP (CD4+ CD8+) cells, respectively.

In FIG. 3, which depicts an analysis of the expression of the hCD4 reporter gene, the mean frequencies of hCD4+ thymocytes found in DN, DP, SP CD4 and SP CD8 cells are (mean plus or minus standard deviation): 21% plus or minus 6.7%, less than 1%, 62% plus or minus 8.4% and 67%. plus or minus 18.1% for line 10 (n=13), and 13% plus or minus 6.0%, less than 1%, 41% plus or minus 12.9% and 68% plus or minus 13.0% for line 7 (n=7). While hCD4 cannot be detected in the DP thymocytes, a very significant fraction of the SP thymocytes expresses the transgene.

Expression of hCD4 was detected in a minor fraction of the DN thymocytes (from 10 to 25% on average). Although these DN and hCD4+ cells represent less than 1% of the total thymocytes, it was important to verify their phenotype in order to determine whether they were precocious DN thymic precursors or mature DN T cells (in that case expressing a TCR/CD3). For this, a triple labeling was carried out using:

a mixture of PE-labeled anti-CD4 and anti-CD8 antibodies, a QR-labeled anti-hCD4 antibody, either an FITC-labeled anti-CD3 antibody, or an FITC-labeled anti-TCR αβ antibody or an FITC-labeled anti-TCR γδ antibody.

As FIG. 4 shows, the double negative hCD4+ thymocytes all consist of cells which are expressing a CD3/TCR receptor; of these cells, ¾ are expressing TCR αβ while ¼ are expressing TCR γδ. This therefore means that the EpCD4 transgene is not expressed in immature DN thymocytes but in mature DN thymocytes which are expressing an antigen receptor.

By contrast, the EpCD4 transgene was found to be expressed in a very substantial fraction of the SP thymocytes, whether their phenotype was CD4+ or CD8+ (FIG. 3).

These results are very surprising and it was not possible to predict them on the basis of currently available information.

From the above it follows that the CD4 minigene is expressed in all peripheral T cells and only on a fraction of the SP thymocytes; the question therefore presents itself of knowing whether this expression in the SP thymocytes correlates with the stages of SP thymocyte differentiation.

In order to answer this question, SP CD4+ CD8− thymocytes were analyzed for the expression of HSA and hCD4 at their surface. This experiment is depicted in FIG. 5 and shows clearly that only the most mature (HSA−) thymocytes express hCD4, while their HSA+ precursors do not express it and there therefore exists a line of descent from hCD4− HSA+ to hCD4+ HSA− in the SP CD4+ thymocytes.

These results demonstrate that expression of the EpCD4 transgene is directly linked to the stage of maturation of the T cells, whether the cell line is CD4+ or CD8+: the expression appears on the most mature SP thymocytes and then persists peripherally.

All in all, this combination of regulatory sequences (promoter+enhancer) controls expression of a reporter gene in only mature T cells and a variable proportion of NK cells. This is an observation which was not foreseeable since previously available information suggested that the combination of these elements would control the expression of a reporter gene from the DP stage onwards. They imply the existence of an additional, as yet unidentified, regulatory element which makes it possible to obtain expression in DP thymocytes and which could be present in the first intron of the CD4 gene.

EXAMPLE 2

Expression of an HSV1-TK Minigene in Mature T Cells from Transgenic Mice:

An EpTK plasmid was constructed; it consists of the same regulatory elements as the previously described EpCD4, that is 3 copies of the murine enhancer, the proT4 human CD4 promoter and the SV40 PolyA signal. It differs from EpCD4 in that the hCD4 cDNA has been replaced with a 1.3 kb fragment containing the DNA encoding HSV1-TK. Transgenic mice were prepared for the purpose of specifically destroying dividing (activated) mature CD4+ and CD8+ T lymphocytes by means of treating with ganciclovir. This destruction also affects DN CD3+ cells, γδ lymphocytes and a proportion of NK cells. On the other hand, this destruction does not affect immature DP thymocyte precursors, which represent the principal population of the thymus. The T lymphocytes which come from the lymphatic ganglia of the transgenic mice are destroyed in vitro by ganciclovir when they are cultured in the presence of a mitogen such as concanavalin A.

A progressive disappearance of a proportion of mature T lymphocytes over time is observed in these transgenic mice which are being used for studying homeostasis and the rate of T lymphocyte renewal when the mice are treated with ganciclovir.

When these transgenic mice suffer an induced deletion of the lymphocytes which respond to a given antigen, a specific antigen tolerance is obtained when ganciclovir is administered in the period surrounding immunization with the antigen.

In these transgenic mice, a graft-versus-host reaction is seen to be controlled during treatment with ganciclovir when this reaction has been induced by a bone marrow graft which is mixed with mature T lymphocytes from EpTK mice. Another result of this is treatment or prevention of the graft-versus-host reaction while preserving the graft-versus-leukemia (GVL) reaction.

In transgenic mice which have been prepared using EpTK-type constructs which have been modified by adding various previously described regulatory elements derived from the human CD4 gene or from CD4 genes of other species, in particular the silencer of the CD4 gene in CD8 lymphocytes and various sequences derived from the first intron of the CD4 gene, T cell populations in which HSV1-TK is expressed when these cell populations are dividing are destroyed by ganciclovir.

Different constructs which contain HSV1-TK and which are placed under the control of the previously described regulatory sequences derived from the CD4 gene of various animal species can be prepared with the aim of producing expression vectors. These vectors are, on the one hand, non-viral vectors and, on the other hand, viral vectors, in particular retroviral vectors or vectors which are derived from AAV or adenovirus. Any of these different vectors can be used for transducing the HSV1-TK gene under control of the various previously described regulatory sequences either into peripheral T lymphocytes which are cultured ex vivo or into bone marrow cells, in particular hematopoietic stem cells. An expected result is the duplication of the specificity of expression which was obtained with the transgenic mice expressing HSV1-TK under the control of the same regulatory sequences as those of the vector, either after its transduction into the peripheral T lymphocytes ex vivo or after its transduction into the hematopoietic stem cells.

EXAMPLE 3
Gene Construct Which Enables Specific Expression to be Obtained in Mature CD4+ T Lymphocytes:

The addition of an, already identified, so-called "CD4 silencer" sequence to the construct containing the CD4 promoter and enhancer makes it possible to prepare a gene construct whose expression is now restricted exclusively to mature CD4+ T lymphocytes in the transgenic mice (FIG. 7). Double negative thymocytes, double positive thymocytes and mature CD8+ T lymphocytes do not express the transgene. As a consequence, this type of construct can be used to transport a transgene exclusively into mature CD4+ T lymphocytes, for example with a view to carrying out a gene therapy, when these regulatory sequences are included in a retroviral vector.

Deletion of Specific T Cell Clones:

The CD4 promoter and CD4 enhancer regulatory sequences which were previously used in the transgenic mice for achieving exclusive expression in mature CD4+ or CD8+ T lymphocytes were used to express an HSV1 TK suicide gene. Transgenic mice were prepared using this gene construct.

The functionality of the gene construct is demonstrated by culturing mature lymphocytes from the ganglia of these transgenic mice in the presence of ganciclovir after having activated the lymphocytes in vitro with a mitogen. The concentrations of ganciclovir which are toxic for the transgenic mouse cells are 100 times lower than those which are required to kill T lymphocytes from non-transgenic mice (FIG. 8a).

With this functionality having been demonstrated, the use for therapeutic applications of expressing an HSV1-TK gene under the control of these regulatory sequences can then be analyzed. The general idea is to destroy the cells when they are activated by the antigen in situations where T lymphocytes are responsible for pathologies. The feasibility of this procedure can be demonstrated by injecting a super-antigen which is known to specifically activate lymphocytes carrying a Vβ7 into transgenic mice and control mice. In either the CD4+ or the CD8+ populations of the control mice, activation with the superantigen SEB results in a doubling of the percentage of the Vβ7 cells. By contrast, when the mice are treated with ganciclovir, there is no change in the number of these cells (FIG. 8b). These results demonstrate that it is possible specifically to destroy cells which are activated by an antigen when the T lymphocytes express the HSV1-TK gene under the control of these regulatory sequences.

Treatment of the Graft-versus-host Reaction:

The functionality of this system for controlling a graft-versus-host reaction was tested. Irradiated mice are reconstituted with bone marrow cells and splenocytes derived from transgenic mice which are expressing the HSV1-TK gene under the control of the CD4 promoter and the CD4 enhancers. This marrow graft is carried out in an allogenic context and under this situation, the splenocytes which are reinjected at the same time as the bone marrow are responsible for a fatal graft-versus-host reaction.

In these experiments, 100% mortality is observed in animals which have received such a marrow graft under allogenic conditions. By contrast, treatment with ganciclovir for 7 days following the marrow graft is sufficient to prevent the development of a graft-versus-host reaction completely. Under these conditions, most of the animals survive the marrow graft without any sign of GVH (FIG. 9).

The table below shows percentage survival in transgenic TK mice based on the results of 3 experiments which lasted from 120 d to 41 d and which were carried out on irradiated mice:

TABLE 2

| GROUPS | BMG+ | CONTROL ANIMALS | TREATED ANIMALS |
| --- | --- | --- | --- |
|  | 84% (n = 13) | 0% (n = 23) | 93% (n = 14) |

The above table shows that while the irradiated mice which are given a bone marrow graft (BMG+) survive, the same mice which are given bone marrow and splenocytes die of GVH (control) unless the splenocytes are derived from transgenic mice and the mice are treated with ganciclovir (treated animals).

The demonstration that this phenomenon is indeed due to destruction of the T lymphocyte clones which are involved in the GVH can be provided by studying the functionality of the lymphocytes in these mice. Thus, when these lymphocytes are withdrawn and activated in mixed lymphocyte reactions either using lymphocytes of the same origin as the recipient or lymphocytes of a third-party origin as the stimulatory cells, it is observed that while there is normal activation against the third-party cells, there is no activation against the recipient cells. These results demonstrate that clones which are specifically capable of recognizing the alloantigens of the recipient, and which are involved in the GVH, have been successfully deleted from the mice which survived the marrow graft.

EXAMPLE 4

Constructs which Contain Different Sequences of the Human CD4 Promoter:

Different gene constructs were prepared in order to ascertain the minimum regulatory sequences, derived from the CD4 gene sequences, which are required for expressing a transgene specifically in T lymphocytes. All these constructs are used for controlling the expression of a reporter gene P. The basic construct contains the 1100 base pairs of the CD4 gene promoter and the CD4 enhancer, which is present in 3 copies. Starting with this construct, other different gene constructs were prepared in accordance with the scheme shown in FIG. 10.

The results of analyzing the expression of the reporter gene after transfecting these different gene constructs of line 4 into Jurkat cells demonstrate (FIG. 11) that:

1) in a general manner, expression is 10 times greater in the presence of the CD4 enhancer than in its absence;
2) the −169+16 fragment of the Pβ1-2C construct is as efficacious as the whole of the 1100 base pair fragment in directing expression of the reporter gene.

In conclusion, these results demonstrate that the short regulatory sequences which are derived from the CD4 gene promoter and enhancer, and which are of a size which is compatible with their use within viral vectors such as retroviral vectors, can be used to obtain specific expression in T lymphocytes.

The same constructs which are derived from CD4 regulatory sequences are not expressed in non-lymphoid CD4+ cells such as, for example, HELA cells.

These experiments also demonstrate that the presence of a single copy of the CD4 enhancer is sufficient for obtaining the expected expression.

What is claimed is:

1. A method of causing selective expression of a nucleic acid in mature T lymphocytes, comprising:
   (i) providing a vector comprising said nucleic acid operably linked to a CD4 enhancer sequence and a CD4 promoter sequence, wherein the vector comprises, in the 5'→3' order:
      a sequence of a CD4 enhancer
      a sequence of a CD4 promoter
      the nucleic acid to be expressed, and
      a polyadenylation signal; and
   (ii) introducing said vector into hematopoietic cells in vitro or ex vivo, said introduction causing expression of said nucleic acid selectively into T lymphcytes matured from said hematopoietic cells.

2. The method of claim 1, wherein the hematopoietic cells comprise hematopoietic stem cells.

3. The method of claim 1, wherein the vector is a viral vector.

4. The method of claim 1, wherein the nucleic acid encodes a toxic polypeptide.

5. The method of claim 1, wherein less than 1% of non-mature lymphocytes express the nucleic acid.

6. The method of claim 4, wherein the polypeptide is a thyrnidine kinase.

7. The method of claim 1, wherein the vector comprises multiple copies of the CD4 enhancer sequence.

8. The method of claim 1, wherein the CD4 enhancer comprises at least one copy of the rnurine CD4 enhancer of SEQ ID No:1.

9. The method of claim 1, wherein the CD4 promoter is selected from the group consisting of the sequence of SEQ ID No: 2, the sequence contained between nucleotides 579 and 1092 of SEQ ID No: 2 and the sequence contained between nucleotides 912 and 1092 of SEQ ID No:2.

10. The method of claim 3, wherein the viral vector is selected from the group consisting of a retroviral vector comprising two LTR sequences, an adenoviral vector and an adenoassociated virus vector.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
TGTTGGGGTT CAAATTTGAG CCCCAGCTGT TAGCCCTCTG CAAAGAAAAA AAAAAAAAAA      60

AAAGAACAAA GGGCCTAGAT TTCCCTTCTG AGCCCCACCC TAAGATGAAG CCTCTTCTTT     120

CAAGGGAGTG GGGTTGGGGT GGAGGCGGAT CCTGTCAGCT TTGCTCTCTC TGTGGCTGGC     180

AGTTTCTCCA AAGGGTAACA GGTGTCAGCT GGCTGAGCCT AGGCTGAACC CTGAGACATG     240

CTACCTCTGT CTTCTCATGG CTGGAGGCAG CCTTTGTAAG TCACAGAAAG TAGCTGAGGG     300

GCTCTGGAAA AAAGACAGCC AGGGTGGAGG TAGATTGGT                            339
```

(2) INFORMATION FOR SEQ ID NO:2:

(i) SEQUENCE CHARACTERISTICS:
        (A) LENGTH: 1096 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
CTGCAGCCTC AACTTCCTGG GCTCAAGCAA TCCTCCCACC TCGGCCTCCT AAAATACTGG      60

GATTATAGGC ATGAGCCACC ACTCCCAGCA CCACTTTTTT CAGACTGGAA AAGAACACTC     120

ACATGTGCAT CTTTAAATGA CACTTGGGCT GTGGTATGGA GAATGGCCAC CAGTGAGTAG     180

GCAGGAGCTG TTGTCCGAGC AAGGGCTGAT ATTGGCATCT TGGATTGGCA TGGTGGCAGT     240
```

-continued

```
AGTGGTAGTG CAGAGTGACT TGGGTAGATT TTGGAGCATT TAGAAGGTAC ATCCACAGGA      300

ACTGGTAAAT AAATACGTGG GAGAAGTTGG GTGAAGGGGG TGTCAAAGAT TACACCCAAT      360

TTATTTTGCT TGGGAAGTTG GTGGATGGTG AGCCCCTCAC TGAGTGAGAA GCCTGGAGAA      420

GCAGGTTTGG AGGGTGGTAG TATGCAGGTG GTATGCATAG TTGGGATGTG TGTTGAGTTT      480

GCTATGTCCG GTGAGCTTCC CAGTGGAGAT GTCCAATGGG CAGACGGATA CTCACATAGA      540

GAGTTCATGG TAGATTCGGG CTAGAGGAAA GCACCTGAGG CCTGGCCAGA GACGCCTAGA      600

GGAACAGAGC CTGGTTAACA GTCACTCCTG GTGTCTCAGA TATTCTCTGC TCAGCCCACG      660

CCCTCTCTTC CACACTGGGC CACCTATAAA GCCTCCACAG ATACCCCTGG GGCACCCACT      720

GGACACAATT GCCCTCAGGG CCCCAGAGCA AGGAGCTGTT TGTGGGCTTA CCACTGCTGT      780

TCCCATATGC CCCCAACTGC CTCCCACTTC TTTCCCCACA GCCTGGTCAG ACATGGCACT      840

ACCACTAATG GAATCTTTCT TGCCATCTTT TTCTTGCCGT TTAACAGTGG CAGTGACACT      900

TGACTCCTGA TTAAGCCTGA TTCTGCTTAA CTTTTTCCCT TGACTTTGGC ATTTTCACTT      960

TGACATGTTC CCTGAGAGCC TGGGGGGTGG GGAACCAGCT CCAGCTGGTG ACGTTTGGGG     1020

CCGGCCCAGG CCTAGGGTGT GGAGGAGCCT TGCCATCGGG CTTCCTGTCT CTCTTCATTT     1080

AAGCACGACT CTGCAG                                                    1096
```